United States Patent

Mouchawar et al.

[11] Patent Number: 5,906,633
[45] Date of Patent: May 25, 1999

[54] SYSTEM FOR DELIVERING ROUNDED LOW PAIN THERAPEUTIC ELECTRICAL WAVEFORMS TO THE HEART

[75] Inventors: Gabriel Mouchawar, Newhall, Calif.; Robert J. Sweeney, Woodbury; Mark W. Kroll, Orono, both of Minn.

[73] Assignee: Pacesetter, Inc., Sylmar, Calif.

[21] Appl. No.: 09/064,422

[22] Filed: Apr. 22, 1998

Related U.S. Application Data

[63] Continuation-in-part of application No. 08/741,184, Oct. 29, 1996, Pat. No. 5,830,236.
[51] Int. Cl.$^6$ ................................................. A61N 1/39
[52] U.S. Cl. ................................. 607/5; 607/63; 128/908
[58] Field of Search ........................... 607/5, 63; 128/908

[56] References Cited

U.S. PATENT DOCUMENTS

| | | | |
|---|---|---|---|
| 2,771,554 | 11/1956 | Grotzel | 607/63 |
| 3,602,754 | 8/1971 | Jares et al. | 607/5 |
| 4,102,348 | 7/1978 | Hihara et al. | 607/63 |
| 5,591,209 | 1/1997 | Kroll | 607/25 |

OTHER PUBLICATIONS

Sharma et al "A Reliable Microprocessor Based Defibrillator Analyzer", *IEEE Transactions on Instrumentation & Measurement*, vol. 1M–31, No. 1 pp. 28–31 copy in 6071005) Mar. 1982.

*Primary Examiner*—William E. Kamm

[57] ABSTRACT

A system for delivering low pain cardioversion shocks to the heart wherein the system provides a waveform to the heart that is biphasic and has rounded leading and trailing edges. The rounded leading and trailing edges are believed to decrease the discomfort experienced by the patient. In one embodiment, the circuit has a two capacitors connected in parallel with each other and with an H-bridge. The two capacitors are connected via a switch that can be closed so as to simultaneously charge one capacitor from the other while simultaneously applying voltage to the H-bridge. The circuit also includes a dump resistor that can be connected in parallel with the capacitors so as to increase the rounding of the trailing edges of the waveform. In another embodiment, controllable switches can also be included so as to be able to connect the capacitors in series and apply a sharp peak defibrillation waveform to the heart.

30 Claims, 9 Drawing Sheets

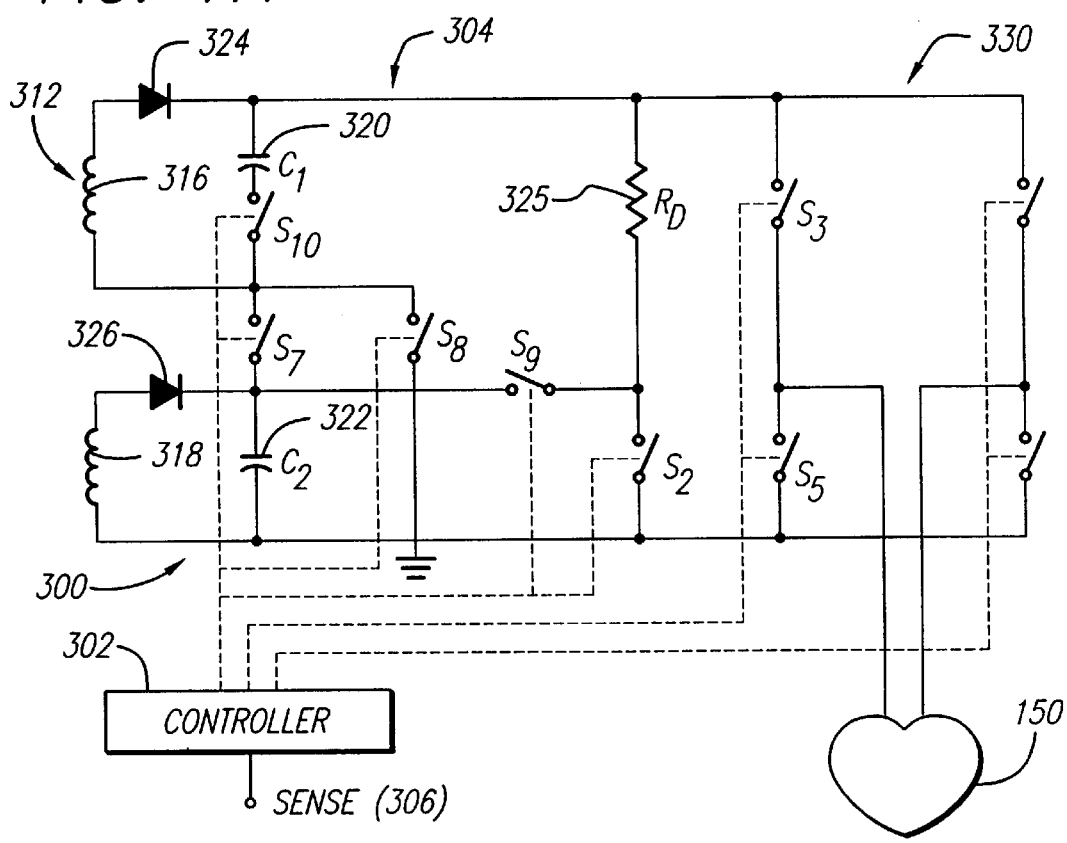
FIG. 7A
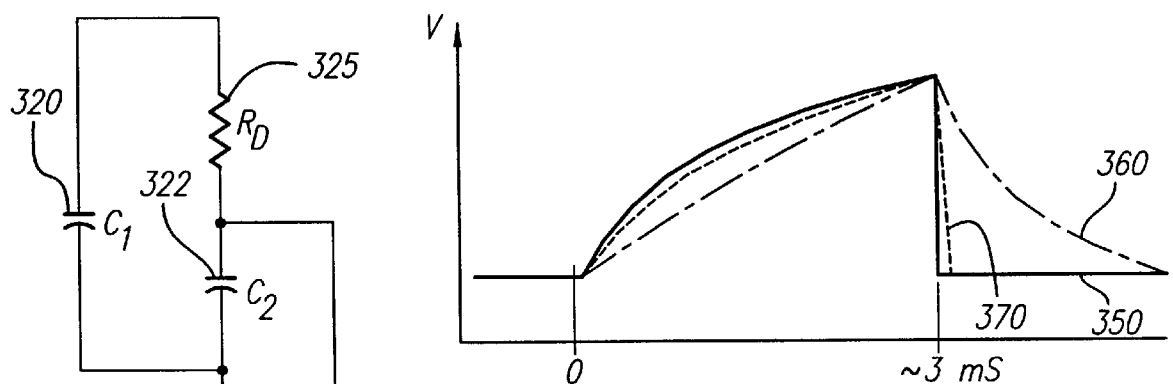
FIG. 7B
FIG. 7C

FINAL VOLTAGE OUTPUT vs. TIME

FIG. 13A
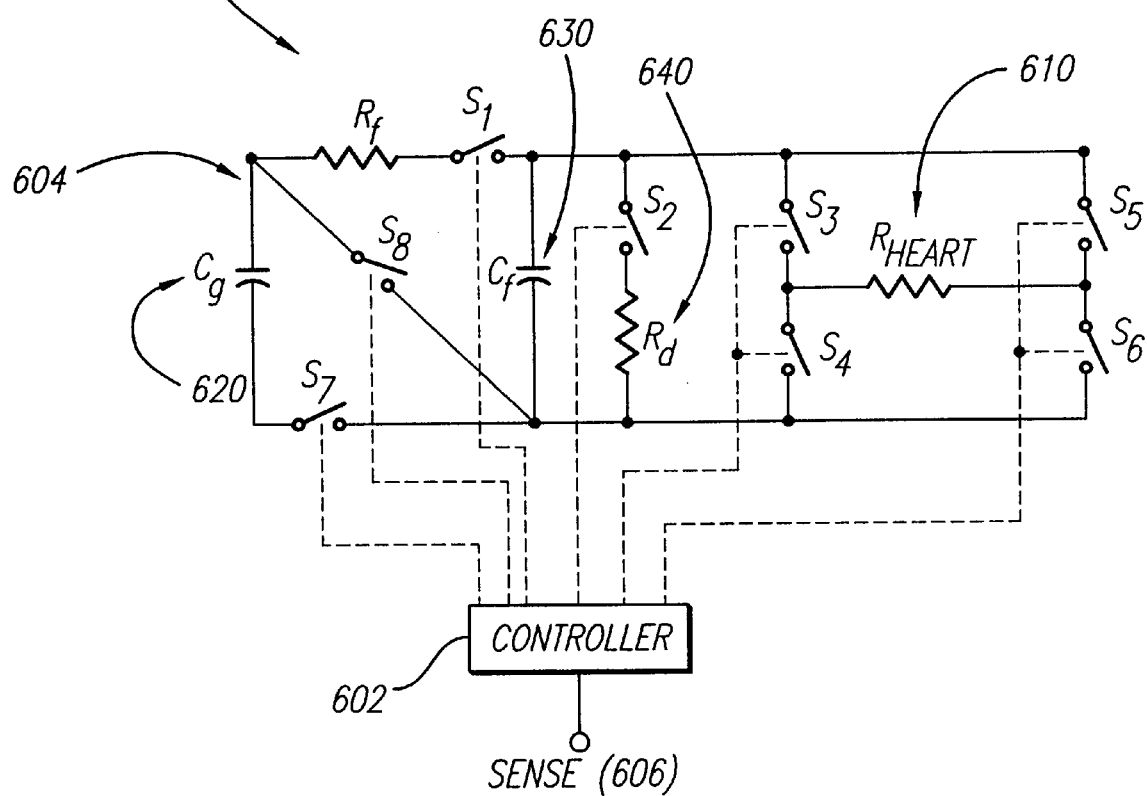
SENSE (606)
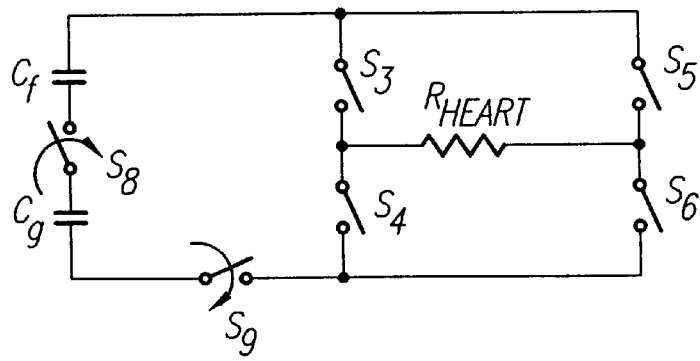
FIG. 13B

SYSTEM FOR DELIVERING ROUNDED LOW PAIN THERAPEUTIC ELECTRICAL WAVEFORMS TO THE HEART

RELATED APPLICATIONS

This application is a continuation-in-part of U.S. patent application Ser. No. 08/741,184, filed Oct. 29, 1996, entitled "SYSTEM FOR DELIVERING LOW PAIN THERAPEUTIC ELECTRICAL WAVEFORMS TO THE HEART," now U.S. Pat. No. 5,830,236.

FIELD OF THE INVENTION

The present invention relates to implantable electrical devices and, more particularly, concerns a system that is capable of providing therapeutic electric shocks to the heart of a patient wherein the therapeutic electric shock is configured to reduce the amount of pain experienced by the patient.

BACKGROUND OF THE INVENTION

Implantable electrical devices, including pacemakers and implantable cardioverter defibrillators (ICD's), are now commonly used in medical practice. These devices are implanted into a patient's body and they provide periodic electrical stimulus, i.e., therapeutic shocks, to the heart to regulate heart function. Typically, pacemakers and ICD's have one or more electrodes that are positioned within the chambers of the heart to deliver the therapeutic shocks.

Implantable cardioverter-defibrillators are an example of a commonly implanted therapeutic device. These devices serve basically two functions. Specifically, the device is configured to be able to provide a high intensity shock to the heart when a control system associated with the ICD detects that the heart is in a state of ventricular fibrillation. The therapeutic shock that is applied to the heart is comprised of a waveform that is configured to be able to end the ventricular fibrillation of the heart and restore the heart to a normal sinus rhythm. Another function that the ICD performs is that of a cardioverter wherein the ICD provides therapeutic shocks to correct ventricular tachycardia or atrial flutter or fibrillation and restore the heart into a normal sinus rhythm or perform shock on T-wave induction. The ICD can also provide therapeutic shocks to correct such conditions as atrial fibrillation. "Shock on T-wave" induction is a function in which a moderate energy shock is delivered during the heart's T-wave to actually cause ventricular fibrillation. This then allows for the testing of the sensory and defibrillation function of the implanted device.

With the typical ICD's of the prior art, the same waveform is applied to the heart regardless of whether the heart is experiencing ventricle fibrillation or atrial fibrillation or ventricle tachycardia. The waveform that is used is generally a biphasic waveform such as the waveform illustrated in FIG. 2. This waveform typically has a peak positive voltage of 750 volts which then exponentially decays to 250 volts at which time a negative voltage is applied to the heart that has a peak voltage of −250 volts which then subsequently exponentially decays to approximately −100 volts. While this waveform is particularly effective at ending episodes of ventricular fibrillation, when this waveform is applied to the patient for cardioversion purposes, to correct ventricle tachycardia or to correct atrial fibrillation, or for shock on T-wave induction, the patient is usually conscious and consequently experiences a very painful sensation associated with the shock. However, when the waveform is being applied for fibrillation purposes the patient is usually (e.g., approximately 70% of the time) rendered unconscious by the fibrillation of the heart and, therefore, does not experience the same painful sensation.

It will be appreciated that a patient equipped with an ICD is likely to experience multiple events of the heart that would require cardioversion. Consequently, the patient is likely to experience very sudden painful shocks as a result of the ICD correcting a cardioversion event at periodic intervals while equipped with the ICD. These very painful shocks have a very serious effect of lowering the quality of life of the patient with the ICD.

In the prior art, there are some implantable electrical devices that are capable of varying the waveform of the therapeutic shock that is applied to the heart. For example, U.S. Pat. No. 5,184,616 to Weiss is an example of an implantable electrical device that is capable of generating varying arbitrarily shaped waveforms to control arrhythmia within the heart. While the device disclosed in this patent is capable of providing different waveforms, this patent fails to disclose a system that is capable of providing a waveform for cardioversion purposes that is specifically configured to successfully end the cardioversion event while minimizing the pain experienced by the patient.

Further, in the existing literature, it is known that different therapeutic waveforms have been used to reduce the pain experienced by the patient in external pacing applications. For example, external non-invasive techniques for stimulation of the heart have been described in an article entitled "Resuscitation of the heart in ventricular standstill by external cardiac stimulation" by P. M. Zoll, N.Engl.J.Med. 247:768 (1952) and in an article entitled "External noninvasive electrical stimulation of the heart" by P. M. Zoll, R. M. Zoll and A. H. Belgard, CRC Crit. Care Med. 9:393 (1981). These articles have described techniques for external stimulation of the heart and have discussed the waveforms that are best suited for external stimulation. A similar, non-invasive pacemaker is described in U.S. Pat. No. 5,018,522 to Rahul that applies a therapeutic shock through the skin that has a waveform that is configured to reduce the amount of pain experienced by the patient. However, in the prior art, there is no teaching of an implantable cardioverter defibrillator that is capable of automatically adjusting the configuration of the waveform that is applied to the heart to decrease the pain experienced by the patient.

Hence, there is a need for an implantable electrical device that is able to provide both therapeutic shocks that are configured to end a fibrillation episode and also therapeutic shocks that are configured to end a cardioversion episode wherein the cardioversion shock is further configured to reduce the pain experienced by the patient. To this end, there is a need for an implantable electric device that does not require a significant amount of additional circuitry in order to be able to achieve this goal. It will be appreciated that with all implantable electrical devices, the size and complexity of the device should be minimized in order to reduce the invasiveness of the implantation procedure and also to enhance the reliability of the device.

SUMMARY OF THE INVENTION

The aforementioned needs are satisfied by the implantable electrical device of the present invention which includes a controller that receives signals indicative of the heart function and provides output control signals to an output circuit that provides therapeutic shocks to the heart. Preferably, the output circuit can be configured to provide a first shock suitable for defibrillation purposes or a second shock suitable for purposes such as cardioversion in response to signals from the controller. In particular, the waveform of the second shock is configured to result in significantly less pain experienced by the patient than the pain that is felt by the patient when the first shock is provided.

In particular, the applicant has initially determined that the response of sensory cells surrounding the heart is significantly faster than the response of cardiac cells. Specifically, high peak voltage waveforms, when applied to the heart, are much more likely to stimulate sensory cells relative to cardiac cells. Consequently, in one embodiment, the ICD of the present invention is configured so as to reduce the peak voltage of the second shock so as to reduce the ratio of response of the sensory cells to the cardiac cells.

The applicant has also determined that sensory cells are less likely to be stimulated for longer time period waveforms. Consequently, in another embodiment, the present invention is configured so as to provide a second shock that is of sufficient duration to reduce the ratio of stimulation of sensory cells to cardiac cells.

More particularly, in one embodiment of the present invention, the output circuit of FIG. 1 includes a first and a second capacitor that are configured to be able to provide the biphasic fibrillation shock of FIG. 2 to the heart. The output circuit also includes a plurality of controllable switches, such as SCR's, MOSFET's, or I.G.B.T.'s that are capable of configuring the output circuit so that the second capacitor is charged via the first capacitor through a resistor, such as a dump resistor, and so that the second capacitor is in parallel with the heart. Consequently, as the second capacitor is charged, the heart sees a voltage waveform that has an inverse exponential rise wherein the time constant for the inverse exponential rise is determined by the value of the resistor and the two capacitors. These values are preferably selected so that the rise time is on the order of three to four milliseconds between a minimum value and a maximum value wherein the maximum value is selected to match that of the cardiac cells. This results in the cardiac cells being stimulated to approximately the same extent that the sensory cells would be stimulated. Consequently, the pain experienced by the patient for cardioversion shocks is reduced as there is less stimulation of the sensory cells located in the path of the cardioversion current, while still achieving the desired cardioversion. In this patent application cardioversion can include all non-defibrillation therapeutic shocks including shocks provided for regulation of ventricular tachycardia, atrial flutter, atrial fibrillation or shock on T-wave induction.

In another embodiment, the voltage is applied to the heart from a defibrillation capacitor with a resistor that is positioned in series with the heart. This results in a long duration therapeutic shock, e.g., on the order of 50 volts for greater than 10 milliseconds, being applied to the heart which results in a lower ratio of stimulation of the sensory cells to the cardiac cells. In this embodiment, there is a controllable switch in parallel with the resistor that shorts out the resistor which can therefore be used to provide a defibrillation shock to the heart wherein the entire voltage of the capacitor is applied directly to the heart. In yet another embodiment, the heart is supplied the voltages via a controllable H-bridge circuit and there is a resistor that is positioned in parallel to the heart during certain configurations of the H-bridge. Alternatively, the switches forming the H-bridge can be configured to short out the resistor so that the entire voltage of the defibrillation capacitor is applied to the heart for defibrillation purposes.

The ICD in this embodiment is therefore capable of selectively applying a defibrillation shock or a cardioversion shock to the heart wherein the output circuit can be configured so that the cardioversion shock is less likely to stimulate the sensory cells. In this embodiment, the cardioversion shock has a longer duration so that the cardiac cells are as likely to be stimulated as the sensory cells. This results in less stimulation of the sensory cells which results in lower pain experienced by the patient.

Alternatively, in another embodiment, a low peak voltage is applied to the heart which is configured to rise to a value configured to stimulate the heart without excess stimulation of the sensory cells.

In yet another embodiment of the present invention, the ICD is adapted to apply a rounded waveform to the heart of the patient. The applicant has reason to believe that a waveform that has both rounded leading edges and rounded trailing edges results in the patient receiving the waveform experiencing less pain. In this embodiment, the circuit providing the waveform is adapted to provide a biphasic waveform wherein the circuit is controllable so that the transitions between the positive portion and the negative portion of the waveform is more rounded.

Further, in another aspect, the circuit is adapted so that the waveform that is being applied to the patient does not include sharp peaks. As discussed above, sharp peak waveforms disproportionately stimulate sensory nerves as compared to cardiac nerves resulting in greater discomfort for the patient. In this embodiment, the circuit is adapted to provide a rounded waveform at the front edge of both the positive and the negative portions of the biphasic waveform. This results in the patient experiencing a biphasic waveform, which is particularly suited for cardioversion purposes or terminating tachycardias, but without the sharp peaks experienced in many prior art biphasic waveforms that cause discomfort for the patient.

It will be appreciated that the present invention can be achieved by modifying a defibrillation output circuit to include a controller and controllable switches wherein the controllable switches are capable of adapting the output circuit to provide the desired cardioversion waveform. Alternatively, the controller and controllable switches can also be used to adapt the output circuit to provide a defibrillation waveform when necessary. These and other objects and advantages of the present invention will become more fully apparent from the following description taken in conjunction with the accompanying drawings.

BRIEF DESCRIPTION OF THE DRAWINGS

FIG. 7A is an electrical schematic illustrating a first embodiment of the ICD of the present invention;

FIG. 7B is a schematic illustrating the equivalent circuit of the ICD shown in FIG. 7A when the circuit is configured to provide the low pain cardioversion shock;

FIG. 7C is a diagram illustrating the positive portion of the cardioversion waveform produced by the circuit of FIG. 7A;

FIG. 13A is an electrical schematic illustrating another embodiment of an ICD, similar to the embodiment of FIG. 10, that is capable of providing either a cardioversion waveform, similar to the waveform of FIG. 11, or a defibrillation waveform, similar to the waveform of FIG. 2, to the heart of the patient; and FIG. 13B is a schematic of an equivalent circuit of the ICD illustrated in FIG. 13A where the ICD is configured to apply a defibrillation waveform.

DETAILED DESCRIPTION OF THE PREFERRED EMBODIMENT

Reference will now be made to the drawings wherein like numerals refer to like parts throughout. The advantages of the present invention will become more fully apparent based upon an understanding of the operation of ICD's of the prior art. Consequently, the operation of a typical prior art ICD and the waveform that it produces is initially described in reference to FIGS. 1 and 2.

Figure 1:
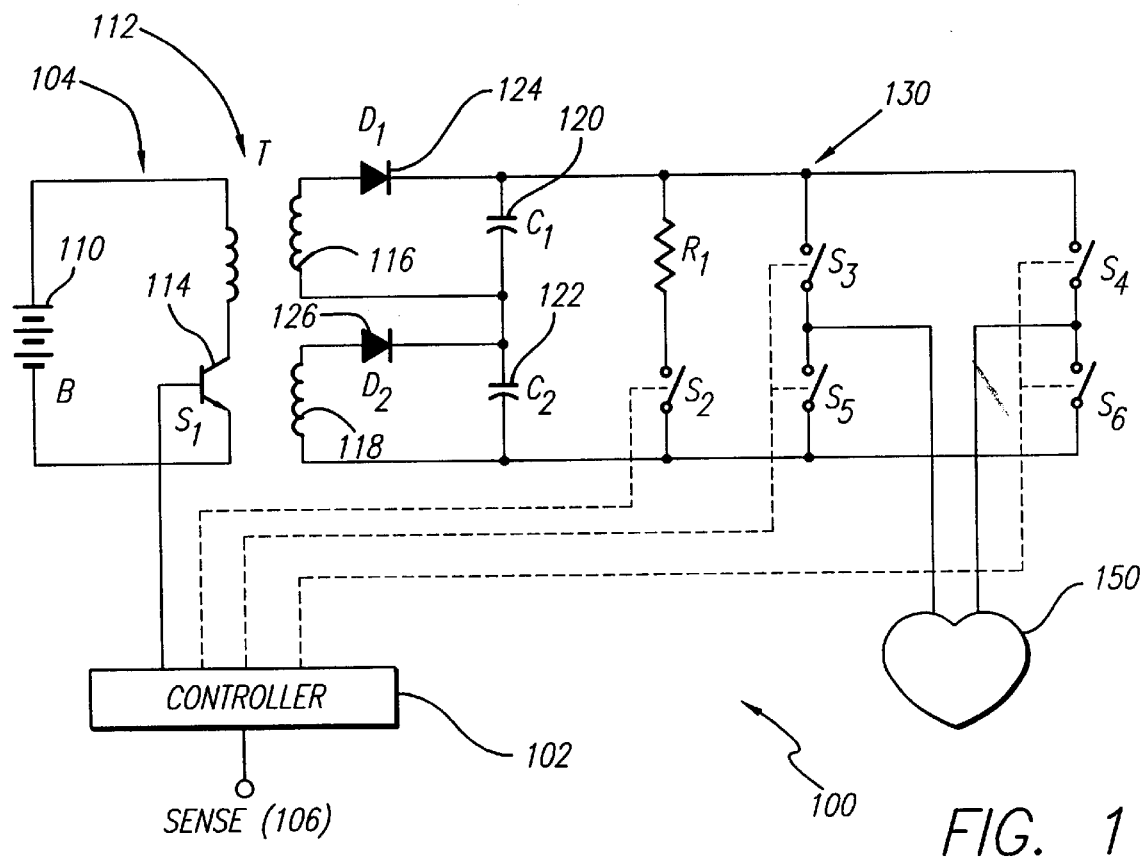
FIG. 1 is an exemplary electrical schematic of an ICD of the prior art.

In particular, FIG. 1 illustrates a conventional ICD 100 of the prior art that is implanted to regulate the function of a heart 150 of a patient. In particular, the typical ICD 100 of the prior art includes a controller 102 and an output circuit 104. The controller 102 preferably receives signals indicative of the function of the heart 150 via a sense input 106 and uses these signals to configure the output circuit 104 to provide an appropriate output signal to the heart 150. Generally, the sense input 106 is comprised of one or more leads that are implanted in the heart 150 that are configured to be able to sense the heart function when not providing a pacing pulse.

The circuit 104 operates as follows: the output circuit 104 generally includes a battery 110 that provides a voltage to the primary winding of a transformer 112 in response to the controller 102 toggling the switch 114 between on and off positions. This results in two secondary windings 116 and 118 respectively charging two capacitors 120 and 122 via two diodes 124 and 126. When these capacitors are charged, the controller 102 induces the switches of an H-bridge 130 to close so as to apply a waveform, such as the waveform illustrated in FIG. 2, to the heart. In particular, the controller preferably initially induces the switches S3 and S6 to close which delivers the positive phase of the shock to the heart 150. Subsequently, the controller then induces the switches S4 and S5 to close to thereby induce the negative portion of the shock.

Figure 2:
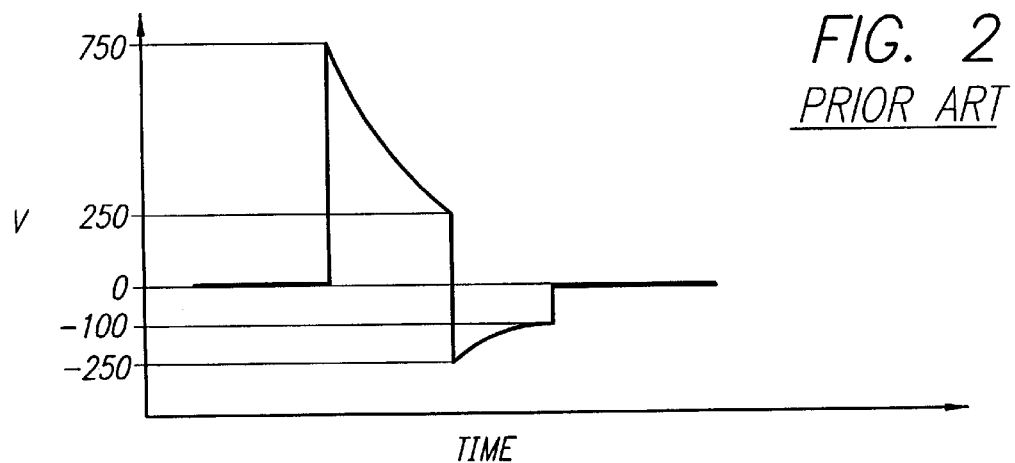
FIG. 2 is an exemplary waveform of a defibrillation shock produced by the circuit of FIG. 1.

FIG. 2 illustrates the preferred defibrillation shock that is produced by the circuit of FIG. 1. In particular, when the switches S3 and S6 are enabled, a voltage of 750 volts is applied to the heart. This voltage exponentially decays to approximately 250 volts over approximately 4 milliseconds at which time the controller 102 activates switches S4 and S5 so that a −250 volt potential is applied to the heart 150. The waveform then decays from −250 volts to approximately −100 volts over approximately 2 milliseconds wherein the switches S4 and S5 are then opened. The waveform of FIG. 2 is recognized as being particularly well suited to correcting ventricular fibrillation of the heart 150.

While the waveform of FIG. 2 is particularly well suited for correcting fibrillation of the ventricle of the heart 150, this waveform when used for other purposes, e.g., for correcting ventricular tachycardia or for purposes such as atrial defibrillation and T-wave induction, results in the patient receiving a very painful sensation.

Figure 3:
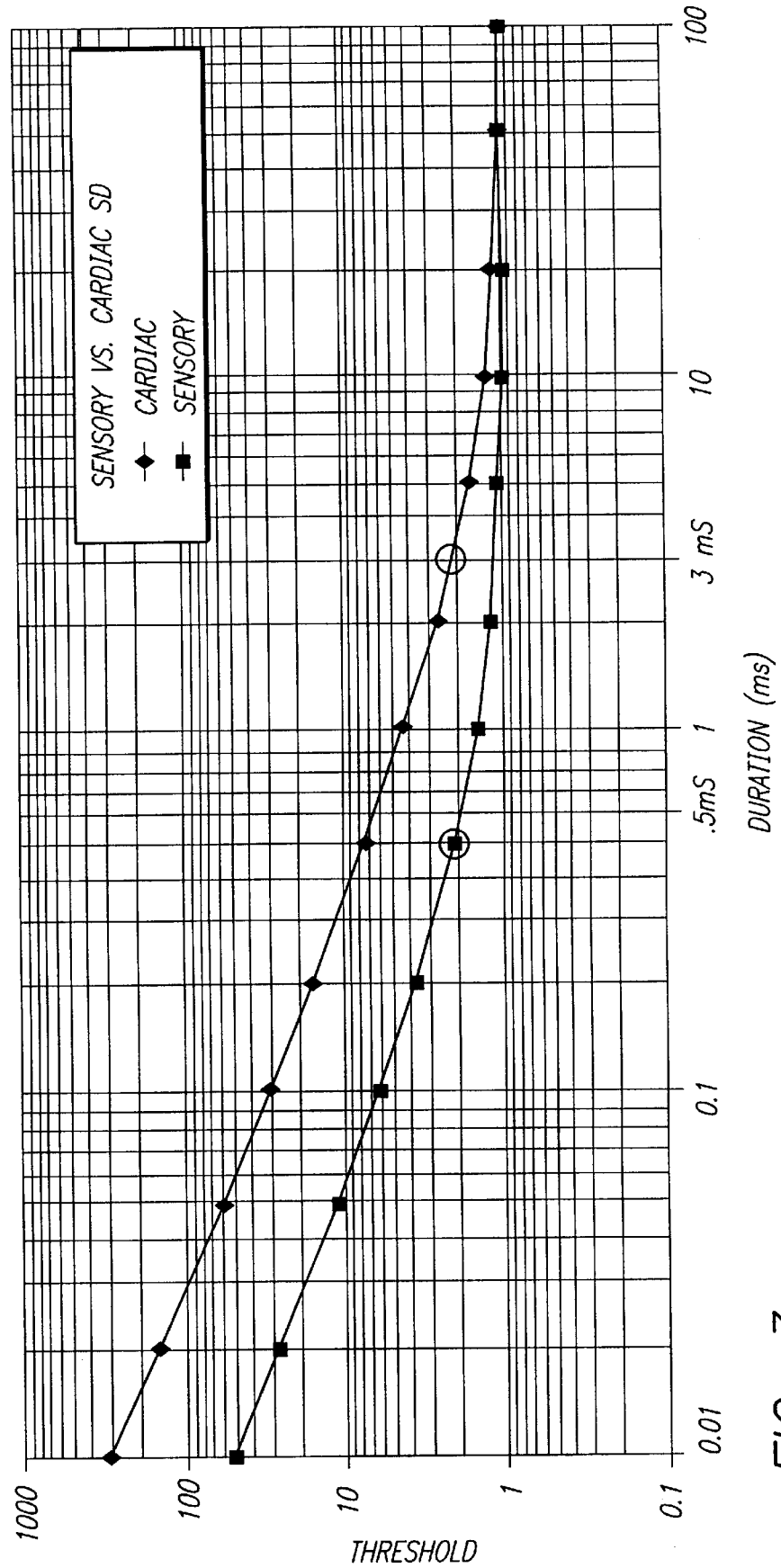
FIG. 3 is a diagram which illustrates the comparative strength duration curves of sensory nerve cells and cardiac nerve cells.

Through mathematical modeling, the applicant has determined that the pain that results from the typical prior art defibrillation shock can be largely explained by the quick response of sensory nerve cells. FIG. 3 is a chart of the normalized strength duration curves of the cardiac cells and the sensory cells which compares the threshold response of cardiac cells and sensory nerve cells for pulse stimuli of different durations. As shown in FIG. 3, the cardioversion/defibrillation chronaxie, i.e., the threshold pulse width on a strength duration curve at twice the rheobase value, for a cardiac cell occurs at approximately 3 milliseconds whereas the chronaxie for a sensory cell is in the range of 0.2 to 0.5 milliseconds. Consequently, the sensory cells respond much faster than the cardiac cells in response to an applied therapeutic shock. These time constants are well known. The time constants for cardiac cells are on the order of 3–4 milliseconds for shocks. However, the typical sensory cell has a time constant on the order of 200–500 $\mu$S. Thus, the sensory cells respond approximately 6–20 times faster than the cardiac cells.

Figure 4:
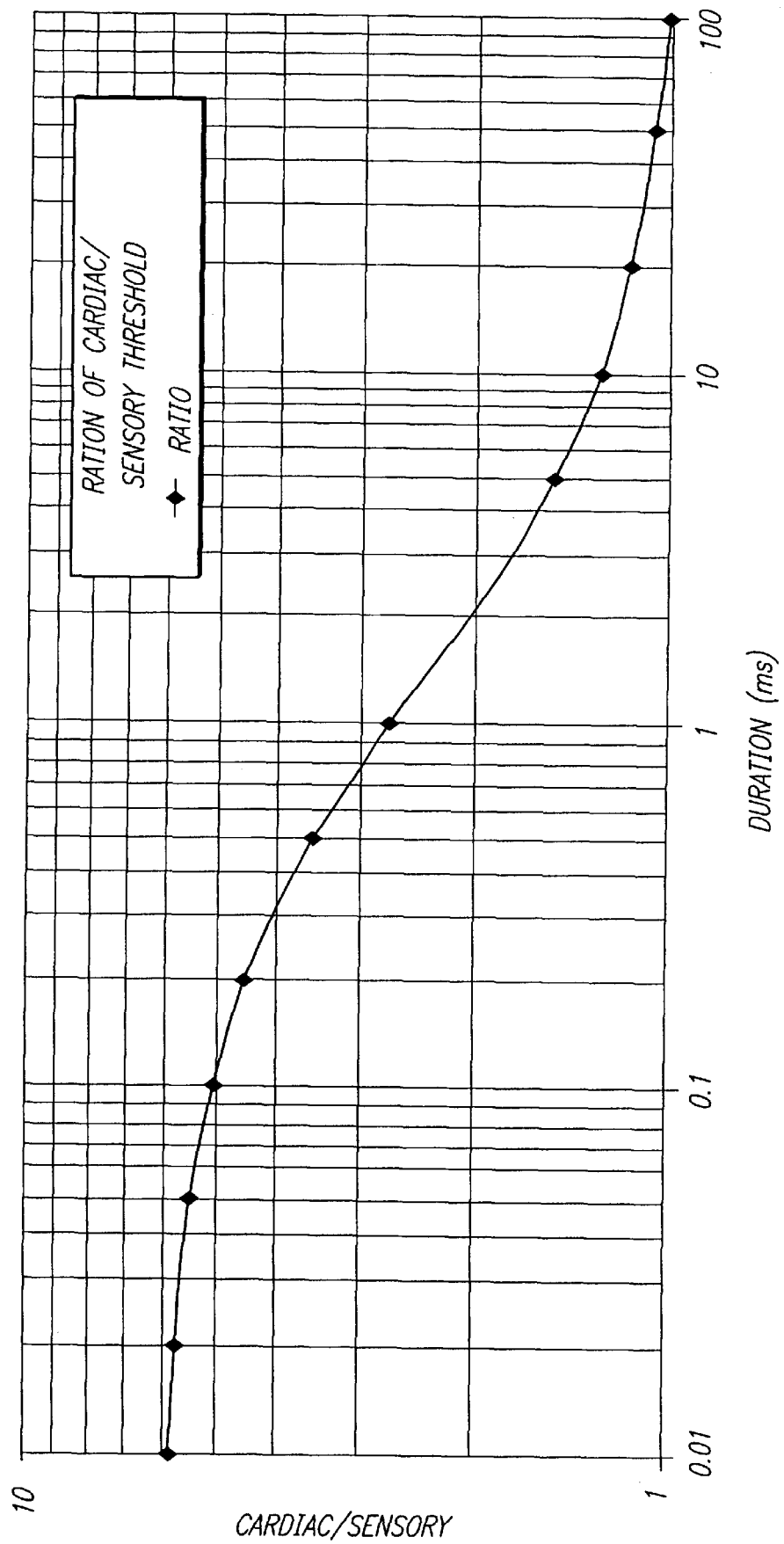
FIG. 4 is a diagram which illustrates the ratio of the threshold value for cardiac cells versus the threshold value for sensory cells in response to an applied electrical signal over time.

Further, as illustrated in FIG. 4, it is understood that if a ratio is calculated for the cardiac/sensory thresholds shown in FIG. 3, that this ratio has two asymptotic values. In particular, for a cardiac chronaxie of 3 milliseconds and sensory chronaxie of 0.5 milliseconds, the ratio between the cardiac/sensory threshold approaches a value of 6 at very short duration pulses. Therefore, for waveforms of very short duration, the sensory cells are six times more likely to be stimulated than the cardiac cells. Conversely, as illustrated in FIG. 4, as the duration of the therapeutic shock increases, e.g., is greater than 10 milliseconds, the ratio approaches an asymptotic value of 1. Therefore, therapeutic shocks that are greater than 10 milliseconds in duration, are equally likely to stimulate cardiac cells as they are to stimulate nerve cells. Therefore, applying a therapeutic shock that has a longer duration, e.g., 10 milliseconds or greater, will result in proportionally less sensory nerve stimulation while still stimulating cardiac cells as compared to shorter pulses.

Figure 5:
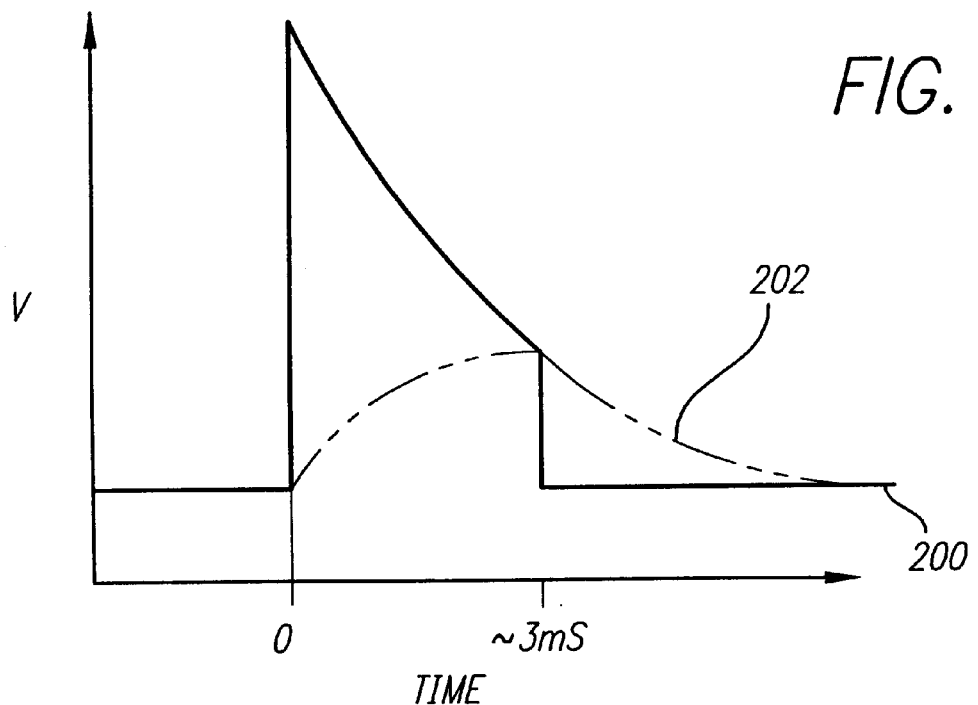
FIG. 5 is a schematic which illustrates the response of the cardiac cells in response to receiving the positive portion of the waveform of FIG. 2.
Figure 6:
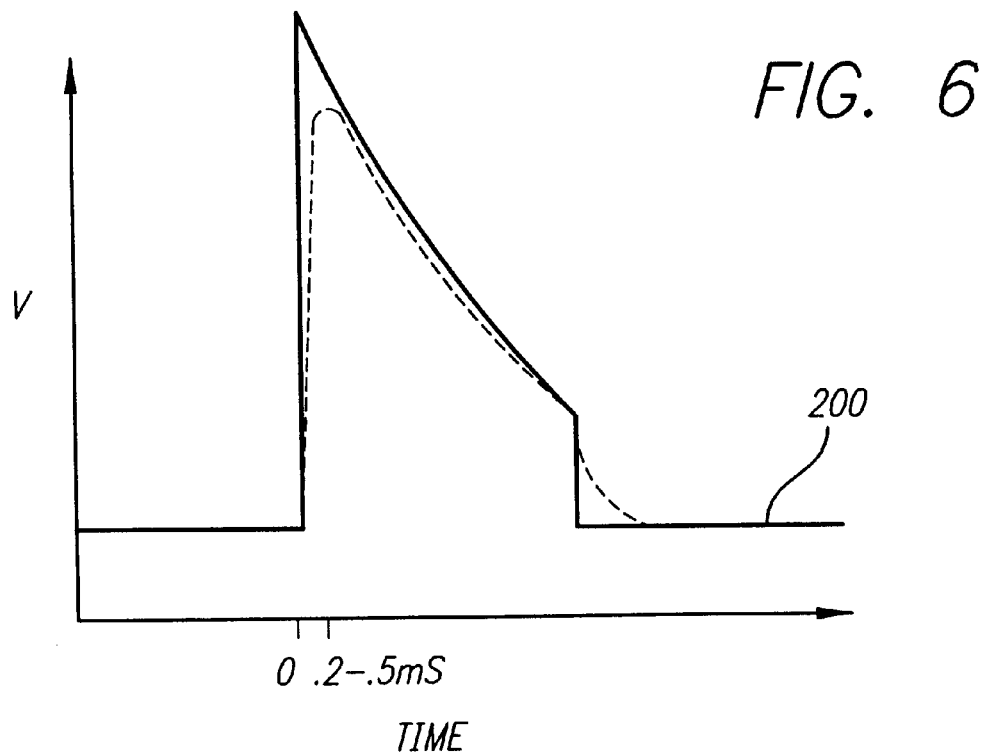
FIG. 6 is a diagram illustrating the response of sensory nerve cells in response to receiving the positive portion of the waveform of FIG. 2.

FIGS. 5 and 6 illustrate another phenomenon that has been identified by the applicant. In particular, in FIG. 5, the positive portion of the defibrillation waveform 200 (FIG. 2) is illustrated. The dashed line 202 illustrates the response of the myocardial cell. At approximately 3–4 milliseconds after the defibrillation waveform 200 has been applied, the myocardial cell fully responds. However, as illustrated in. FIG. 6, in response to the therapeutic waveform 200, the sensory nerve cells, as indicated by the dotted line 204, have responded nearly simultaneously to the application waveform 200. Consequently, almost the entire positive waveform 200 of the therapeutic shock shown in FIG. 2 stimulates the sensory nerve cells even though the cardiac cells will not respond until the positive waveform is almost completed.

Thus, it can be said that the pain is determined by the peak voltage of the shock. Hence, when the defibrillation waveform of FIG. 2 is used for cardioversion purposes, the patient experiences a significant amount of pain as a result of the undesired stimulation of the sensory cells. Since the sensory cells are being stimulated without a corresponding stimulation in the cardiac cells, the patient is in effect experiencing a pain penalty as a result of using the defibrillation waveform for cardioversion purposes.

FIG. 7A is an electrical schematic of one embodiment of an ICD 300 that is configured to apply a cardioversion waveform to the heart that is of the gentle, rounded shape so that the cardiac cells are stimulated while minimizing excess stimulation of the sensory cells surrounding the heart. FIG. 7A simply illustrates the output stage of an output circuit 304. The circuit 304 includes a battery 110 that feeds the primary winding of a transformer 312 in response to manipulation of a switch (not shown) similar to the transistor switch 114 shown in FIG. 1. This results in the secondary windings 316 and 318 charging a first capacitor 320 and a second capacitor 322 through diodes 324 and 326 respectively when a switch S10 is in a closed position. Once the capacitors 320 and 322 are charged, controllable switches S3–S6 in the H-bridge 330 and S7 and S10 can then be closed to apply the defibrillation waveform of FIG. 2 in the manner described above in reference to FIG. 1. Hence, the ICD circuit 300 is capable of applying a biphasic defibrillation waveform to the heart 150 of the patient.

However, the output circuit 304 also includes a plurality of switches S7–S10 that are controllable by the controller 302. In particular, the controller 302 manipulates the switches S7–S10 to apply the gentle, rounded cardioversion waveform 320 (shown in FIG. 7C) that is configured to stimulate the cardiac cells of the heart 150 while minimizing any excess stimulation of the sensory cells surrounding the heart 150. The switches S7–S10 are preferably comprised of SCR's or transistors that are operable by control signals emanating from the controller 302.

In particular, when the controller 302 receives a signal on the sense input 306 indicating the need for the cardioversion waveform 350, the controller opens the switch S10, which opens the circuit to capacitor 320. The controller 302 induces the primary winding of the transformer 312 to be energized from the battery 110 (FIG. 1). This results in only the capacitor 322 being charged via the diode 326. After the capacitor 322 is charged, the controller 302 then opens S7 and closes switch S8 which connects the capacitor 320 to ground. Further, the controller also closes a switch S9 and the switch S10 which connects the capacitor 320 to ground and also to the capacitor 322 through a resistor 325. The controller 302 also closes two of the switches in the H-bridge 330, i.e., switches S3 and S6, so that the equivalent circuit shown in FIG. 7B is produced.

In particular, the heart 150 is now in parallel with the uncharged capacitor 320 and the capacitor 322 in series with the resistor 325. This results in the capacitor 322 discharging to thereby charge the capacitor 320 through the resistor 325. It will be appreciated that the capacitor 320 is charged in an inverse exponential fashion as shown by the waveform 350 in FIG. 7C. In particular, the component values of the capacitors 322 and 320 and the resistor 325 are selected so that the waveform seen by the heart 150 charges for approximately 3 milliseconds to a threshold value that is selected to stimulate the cardiac cells of the heart 150. After three milliseconds, the controller 302 opens the switches S3 and S6 thereby removing the applied voltage to the heart 150.

FIG. 7C illustrates that the waveform 350 produced by the equivalent circuit of FIG. 7B results in a stimulation of the cardiac cells as represented by waveform 360 and with the sensory cell response 370 more closely tracking the waveform 350. This results in a reduction in the stimulation of the sensory cells as compared to the defibrillation waveform 250 which further results in less pain experienced by the patient. Consequently, the myocardial cells of the heart 150 are adequately stimulated for cardioversion purposes but do not result in excess stimulation of the sensory cells.

It will be appreciated by reference to FIG. 7A that the ICD 300 of this embodiment is capable of providing both the waveform 250 of FIG. 2 and the waveform 350 of FIG. 7C. Further, the functionality of providing these two disparate waveforms is achieved through the addition of the controllable switches S7–S10. It will be appreciated that the ICD 300 achieves this greater functionality without requiring a significant amount of space for additional components.

In the embodiment shown in FIG. 7A, the resistor that is used to charge the capacitor 320 is the dump resistor 325. In the event that the charge in the capacitors 320 and 322 may want to be dumped without being applied to the heart, the controller is configured to enable the switches S2 and S10 and S7 while disabling the switches S8 and S9 which will result in the store charge in the capacitors 320 and 322 being dissipated across the resistor 325 in a manner and for purposes that are well understood in the art. It will be appreciated that, while the use of the dump resistor 325 as a resistor configured for applying the cardioversion waveform is efficient, two separate resistors can be used, one for dumping and one for producing the cardioversion waveform, without departing from the spirit of the present invention.

It will be further appreciated that the exact configuration of the waveform 350 (FIG. 7C) can be tuned by adjusting the value of the resistor 325. A typical value for this resistor 325 would be between 10–200 ohms. It will be further appreciated that the waveform 350 can be extended in length by opening and closing the switch S9 after the switches S3 and S6 are closed. This results in a pulsating current being applied to the capacitor 320 which then smooths (low pass filters) the waveform to increase the effective time constant and, hence, the duration. Further, a person of ordinary skill in the art will appreciate that the circuit of FIG. 7A can be modified slightly so that a biphasic voltage can be applied to the heart 150 with a similar inverse exponential rise on both the positive and negative sides of the waveform. This type of waveform can also be used for various beneficial therapeutic purposes.

Figure 8A:
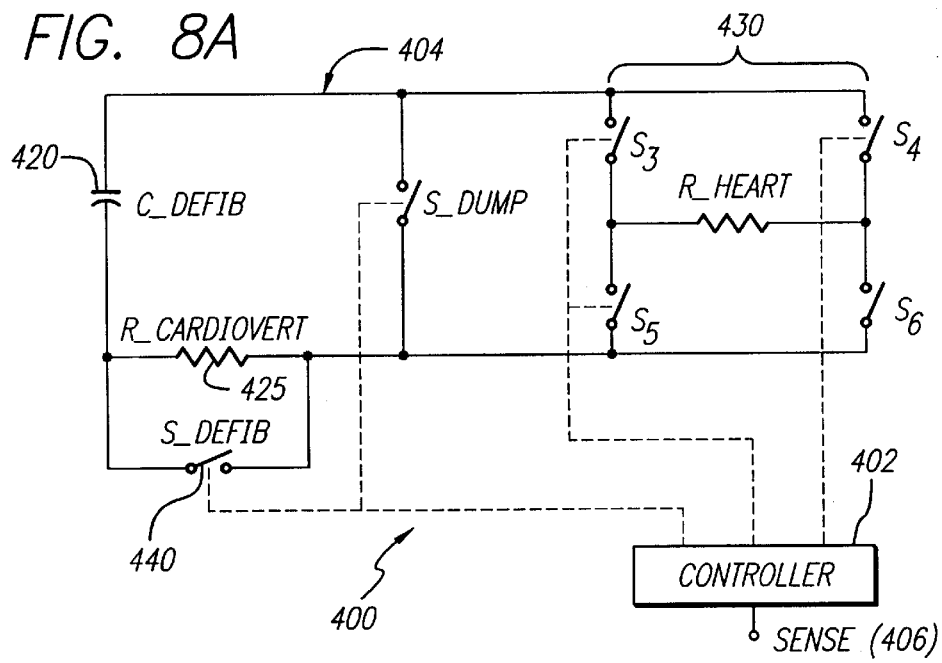
FIG. 8A is an electrical schematic of another embodiment of the ICD of the present invention.

FIG. 8A is a simplified schematic of another embodiment of an ICD 400 that is capable of providing both a defibrillation shock similar to the waveform shown in FIG. 2 and a longer duration cardioversion shock to the heart 150. In particular, the ICD 400 includes a controller 402, which receives a sense input 406 in the same manner as described above, and an output circuit 404. In FIG. 8A, the output circuit 404 includes one or more defibrillation capacitors 420 which are preferably charged in a similar manner as described hereinabove. Further, the output circuit 404 includes an H-bridge 430 comprised of switches S3–S6 that apply the therapeutic shock to the heart 150 which in FIG. 8A is represented by a resistor.

Figure 8B:
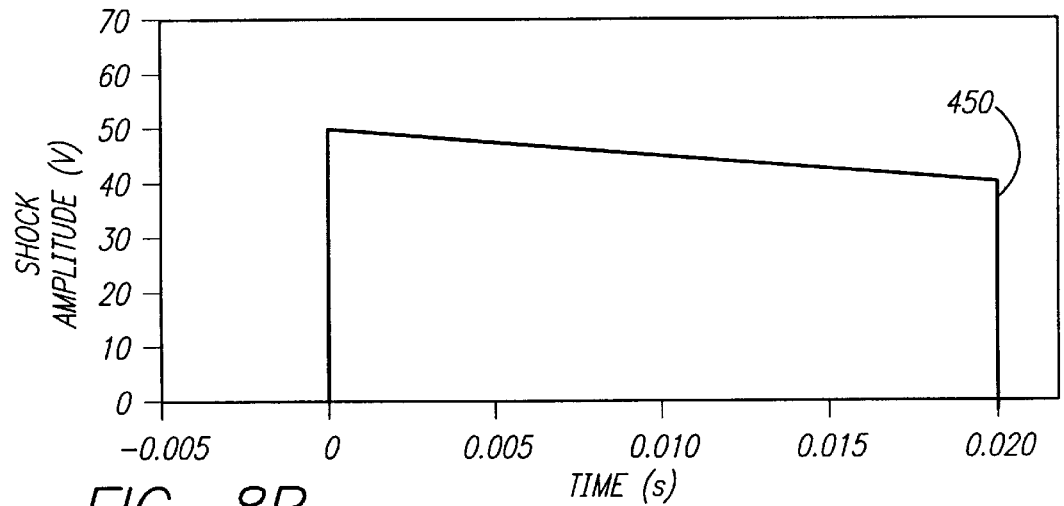
FIG. 8B is a diagram illustrating the waveform produced by the circuit of FIG. 8A.

A cardioversion resistor 425 is connected in series between the capacitor 420 and the H-bridge 430. Further, there is a defibrillation switch 440 that is connected across the resistor 425 so that when the switch 440 is closed by the controller 402, and the H-bridge is closed across the heart 150, a defibrillation waveform, such as the waveform 250 shown in FIG. 2, can be applied to the heart 150. Alternatively, when the H-bridge 430 is closed by the controller 402 manipulating two of the switches S3–S6 to apply the voltage in the capacitor 420 and the controller opens the switch 440, a cardioversion waveform 450 shown in FIG. 8B is applied to the heart 150.

In this embodiment, the capacitor 420 is capable of storing up to 750 volts. However, for a long duration pulse (e.g., a pulse of 10–20 milliseconds) only approximately 45 volts is needed to perform cardioversion. Consequently, the resistance of the cardioversion resistor 425 is selected so that the total voltage that is seen by the heart is approximately 40–50 volts. Further, the tilt or decline of the waveform seen by the heart is less as a result of the increase in resistance since the time constant of the discharge of the capacitor 420 is equal to the resistance of the heart 150 plus the resistance of the resistor 425 times the capacitance of the capacitor 420.

Therefore, a cardioversion waveform 450 can be applied to the heart 150 that is relatively long in duration with a gradual decrease in amplitude. This results in lowered stimulation of the sensory cells surrounding the heart while maintaining a sufficient degree of stimulation of the cardiac cells to result in cardioversion. In particular, reference to FIGS. 3 and 4 illustrate that at time lengths greater than 10 milliseconds, the waveform is as likely to stimulate the cardiac cells as the sensory cells. Consequently, applying the waveform 450, which is approximately 20 milliseconds long, results is less stimulation of sensory cells as the waveform 250 shown in FIG. 2. Consequently, the cardiac cells of the heart 150 are adequately stimulated for cardioversion purposes, but the pain experienced by the patient is decreased.

In the event that the controller 402 receives a signal via the sense input 406 indicating the need for a defibrillation shock, the controller 402 can close the defibrillation switch 440 and close the switches S3–S6 of the H-bridge 430 in the manner described above so that substantially the entire voltage of the capacitor 420 is applied across the heart in a waveform that is similar in shape to the waveform 250 shown in FIG. 2. Consequently, the ICD 400 is capable of providing both a defibrillation shock and a cardioversion shock wherein the cardioversion shock is configured to result in less pain to the patient.

Figure 9:
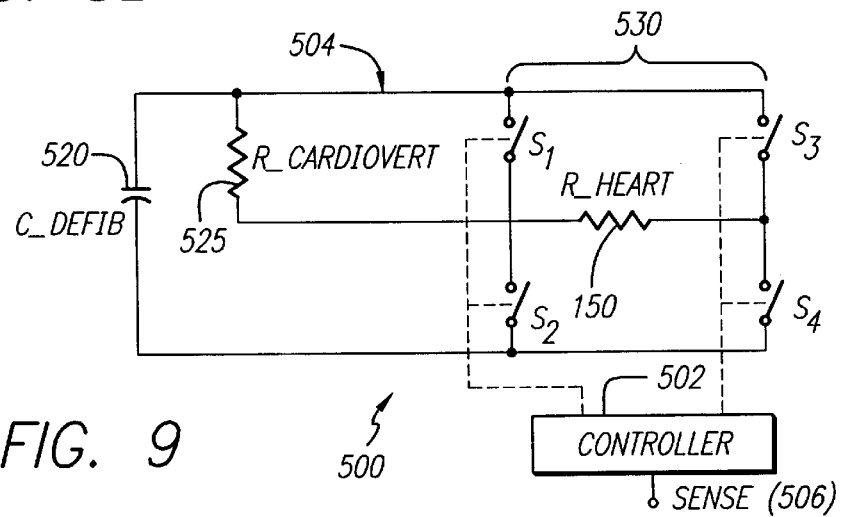
FIG. 9 is an electrical schematic illustrating yet another embodiment of the ICD of the present invention.

FIG. 9 is yet another embodiment of an ICD 500 that is capable of providing both a defibrillation shock of high amplitude and relatively shorter wave pulses and a cardioversion shock of comparatively low amplitude for a relatively long time period in the manner described above in conjunction with the description of the ICD 400 described in reference to FIGS. 8A and 8B. In particular, the schematic illustrated in FIG. 9 is a simplified schematic of an ICD 500 that includes a controller 502 which receives a sense input 506 in the same manner as described above. The ICD 500 includes an output circuit 504 which includes one or more defibrillation capacitors 520 that is charged in the manner described above. Further, there is an H-bridge 530 comprised of four switches, S1–S4, that are controlled by the controller 502 to apply the voltage to the heart 150. It will be appreciated that when the switches S1–S3 are open but the switch S4 is closed, then a cardioversion wave pulse similar to the wave pulse shown in FIG. 8B is applied across the heart 150. Alternatively, when the controller 502 receives a signal on the sense input 506 indicating that a defibrillation shock should be applied to the heart 150, the switches S1 and S4 can be closed thereby shorting out the cardioversion resistor 525 so that the positive portion of the shock can be applied to the heart 150. Subsequently, switches S3 and S2 are then closed so that the negative portion of the waveform 250 can be applied across the heart 150. In this manner, the ICD 500 is capable of providing both a biphasic defibrillation shock and a cardioversion shock that is configured to reduce the pain experienced by the patient depending upon the condition of the heart sensed by the controller 502. In both embodiments shown in FIG. 8A and FIG. 9, R-Cardiovert is the dump resistor.

From the foregoing, it should be apparent that the preferred embodiments of the present invention are capable of providing both fibrillation shocks and cardioversion shocks to the heart depending upon the conditions sensed by a controller. The cardioversion shock is configured so that the stimulation of the sensory cells surrounding the heart is minimized. This reduces the pain experienced by the patient during such activities such as ventricular cardioversion, atrial cardioversion, atrial defibrillation, defibrillation, and T-wave induction. This decrease in pain results in a higher quality of life for the patient.

Figure 10:
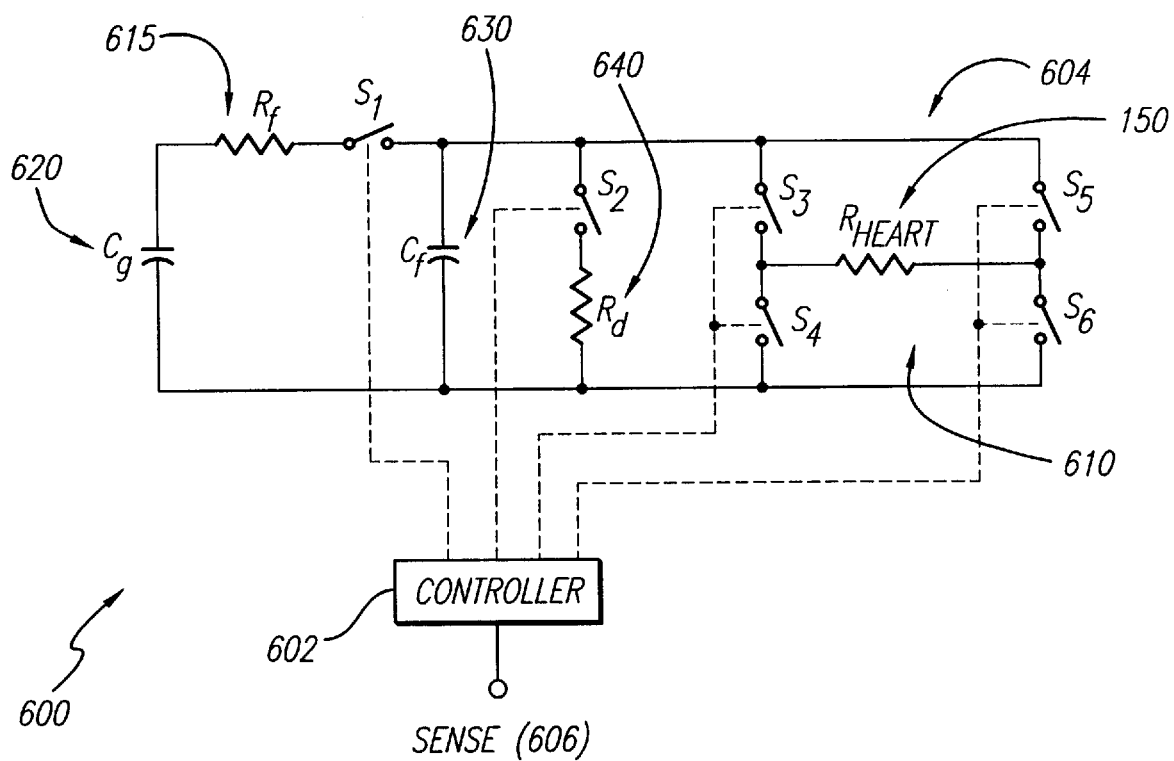
FIG. 10 is an electrical schematic illustrating yet another embodiment of the ICD of the present invention which is adapted to provide a low pain cardioversion waveform to a patient.

FIG. 10 is yet another embodiment of an ICD 600 that is capable of providing a defibrillation or cardioversion waveform that is adapted so that the patient experiences less pain upon delivery of the waveform. In particular, the schematic shown in FIG. 10 is a simplified schematic of an ICD 600 that includes a controller 602 and an output circuit 604 similar to the controller and output circuits described above. The controller 602 receives a sense input 606 from a sensor implanted adjacent the heart and uses the signal from the sense input 606 to deliver cardioversion or defibrillation therapy in a manner known in the art.

The output circuit 604 includes an H-bridge 610 comprised of switches S3–S6 that is adapted to provide a biphasic waveform to the heart in a well known manner. The output circuit 604 also include one or more defibrillation or cardioversion capacitors Cg 620 that is connected in parallel with the H-bridge 604 where the positive node of the capacitor Cg 620 is connected to the switches S3 and S5 of the H-bridge 610 via a resistor Rf 615 and a switch S1. The output circuit 604 in this embodiment also includes a capacitor Cf 630 that is connected between the switch S1 and the H-bridge 610 so as to be in parallel with the capacitor Cg 620 and the H-bridge 610. Further, the output circuit 604 also includes a dump resistor Rd 640 that is connected via a switch S2 to the switch S1 so as to also be in parallel with the capacitors Cg 620, Cf 630 and the H-bridge 610.

Figure 11:
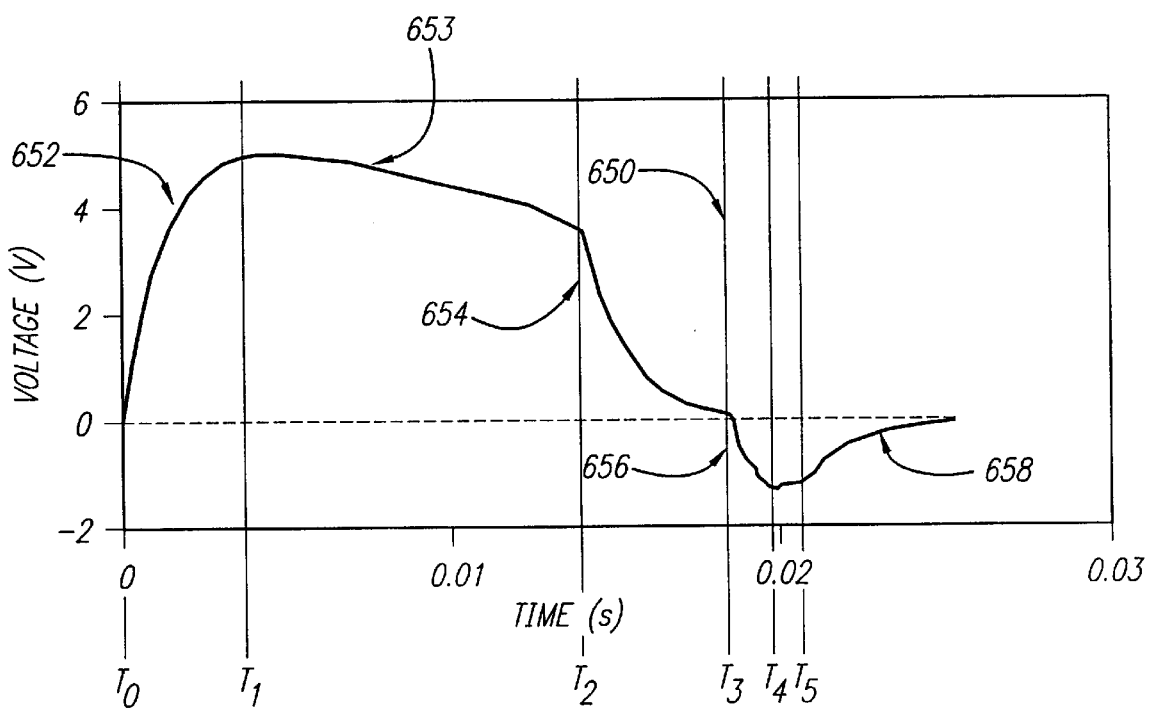
FIG. 11 is a diagram illustrating one embodiment of a cardioversion waveform produced by the circuit of FIG. 10.

The switches S1–S6 are all controlled by the controller 602 so that the controller 602 can induce the output circuit 602 to provide the rounded biphasic cardioversion waveform 650 of FIG. 11 to be applied to the heart 150. Referring now to FIG. 11, the biphasic waveform 650 will now be described in greater detail. Specifically, the biphasic waveform 650 is adapted to have both a rounded leading edge 652 and a rounded trailing edge 654 on the positive portion waveform, as well as a rounded leading edge 656 and a rounded trailing edge 658 on the negative portion of the waveform. It is believed by the Applicant that a waveform having rounded edges is likely to result in less discomfort for the patient who is undergoing atrial defibrillation or cardioversion therapy in a conscious state.

Figure 12A:
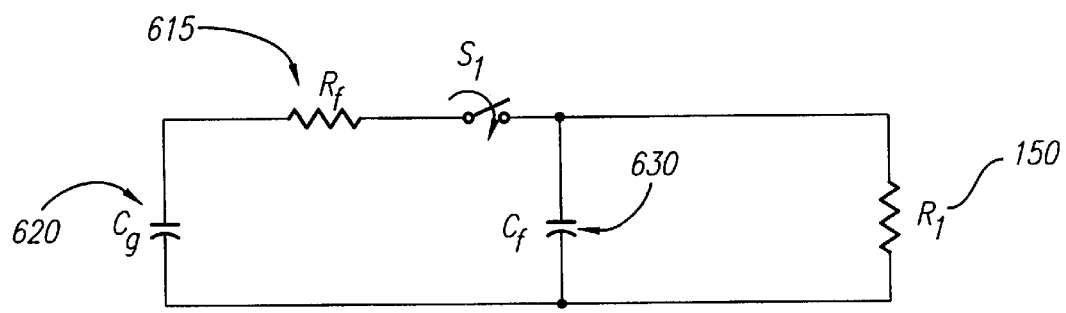
FIGS. 12A and 12B are schematics illustrating equivalent circuits of the ICD shown in FIG. 10.

The controller 602 produces the waveform 650 by opening and closing the switches S1–S6 in the following manner. Specifically, at a time T0, when the controller 602 has determined to apply the waveform 650 to the heart 150, the capacitor Cg 620 is initially charged and the controller 602 then closes the switches S1, S3 and S6 while leaving the switches S2, S5, and S4 open. This results in the controller 602 configuring the output circuit 604 into the equivalent circuit 660 shown in FIG. 12A.

Specifically, the heart 150, represented by the resistor R1, is connected to the positive node of the capacitor Cg 620 via the resistor Rf 615 and the closed switch S1. The capacitor Cf 630 is connected to the resistor Rf 615 so as to be connected in parallel to the heart R1 150 and the capacitor Cg 620. The capacitor Cf 630 is initially not charged but is now charged as the capacitor Cg 620 discharges through the resistor Rf 615 and the heart R1 150. The charging of the capacitor Cg 630 while simultaneously providing energy to the heart 150 results in positive portion of the waveform having the rounded leading edge 652 (FIG. 11).

Once the capacitor Cg 630 has discharged to a time T1, Switch S1 is opened which results in the capacitor Cg 620 being disconnected from the heart 150 and the charged capacitor Cf 630 discharging through the heart R1 150. This results in the slowly declining portion 653 of the positive portion of the waveform 650. It will be appreciated that the capacitor Cg can be selected so that the waveform is rather long in duration so as to decrease the stimulation of the sensory nerves while still stimulating the cardiac nerves in the same manner as discussed above in reference to the embodiment described in connection with FIGS. 8A and 8B.

Figure 12B:
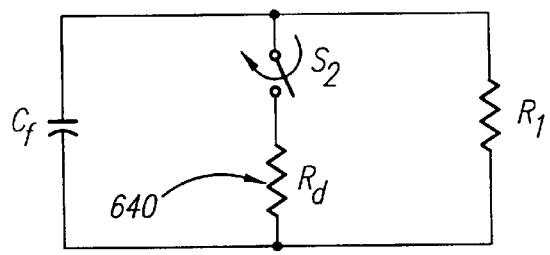

Once a time T2 is reached, the controller 602 then closes switch S2 so as to configure the output circuit 604 into the equivalent circuit shown in FIG. 12B. At this point, the stored energy in the capacitor Cg 630 is being discharged through both the dump resistor 640 and the heart 150 thereby resulting in an exponential decay of the applied voltage. The dump resistor 640 is preferably selected so as to have a significantly lower resistance value so that more current is discharged through the dump resistor 640 than through the heart 150 thereby enhancing the rounded trailing edge 654 of the waveform 650 as shown in FIG. 11. As discussed above, since the trailing edge 654 is rounded, the waveform 650 is likely to produce less discomfort for the patient than the sharp edged waveforms illustrated previously, while still providing substantially the same cardioversion benefits.

At time T3, all of the switches S1–S6 are opened so as to start the negative portion of the waveform 650 at zero. Subsequently, the switches S5 and S4 are closed in the H-bridge 610 so that the negative portion of the waveform 650 can be applied to the heart 150 and the switches S1 and S2 are manipulated in the above-described fashion so that the negative portion of the waveform 650 can also have rounded leading and trailing edges. Specifically, the switch S1 is then closed at a time T3 so that the capacitor Cg 620 is discharged via the resistor Rf 615 into the heart 150 and the capacitor Cf 630 in the same manner as described above. This results in the leading edge 656 of the negative portion of the waveform 650 being rounded in the manner shown in FIG. 11. At a time T4, the switch S1 is opened so that the capacitor Cg 630 is disconnected from the H-bridge and the capacitor Cf 630 is discharged via the heart 150. Subsequently, at a time T5, the switch S2 is closed so that the capacitor Cf 630 discharges through both the heart 150 and the dump resistor 640 resulting in the enhanced rounded trailing edge 658 of the negative portion of the waveform 650 shown in FIG. 11.

Hence, the output circuit 604 is capable of providing a biphasic cardioversion waveform having rounded leading and trailing edges so as to reduce the discomfort experienced by the patient while still providing the cardioversion benefits of a biphasic waveform. The output circuit 604 can be adapted to be used with the previously described output circuits so that the output circuits are capable of providing either a defibrillation shock or a long duration cardioversion waveform. The rounding of the cardioversion waveform edges is likely to result is less discomfort and can be combined with long duration waveforms to further reduce the discomfort.

In particular, FIGS. 13A and 13B illustrate how the ICD 600 can be modified so as to be able to provide both the rounded cardioversion waveform of FIG. 11 and a biphasic defibrillation waveform similar to the waveform illustrated in FIG. 2. In particular, the addition of a controllable switch S8 and a controllable switch S9 to the output circuit 604 as shown in FIG. 13A so as to be able to connect the capacitors Cg 620 and Cf 630 in series allows the output circuit 604 to be configured to be able to provide a biphasic defibrillation waveform similar to the waveform illustrated in FIG. 2.

As shown in FIG. 13A, the controllable switch S8 is connected between the positive node of the capacitor Cg 620 and the negative node of the capacitor Cf 630 so that when the controller 602 closes the switch S8, the capacitors Cg 620 and Cf 630 are connected in series. Moreover, the controllable switch S9 is connected between the negative node of the capacitor Cg 620 and the H-bridge 610.

The controller 602 can configure the output circuit 604 into the equivalent circuit shown in FIG. 13B by closing the switches S8 and S9 while leaving the switches S1 and S2 open. The H-bridge 610 then receive the sum of the stored voltage in the capacitors Cg 620 and Cf 630. As there are no resistors or parallel capacitors, the sum of the stored voltages can be applied across the heart 150 in a biphasic waveform by initially closing the switches S3 and S6 of the bridge 610 while leaving S4 and S5 of the H-bridge 610 open and then opening the switches S3 and S6 and closing the switches S4 and S5 in a well known manner.

Hence, the ICD 600 can be adapted to provide only a waveform similar to the waveform shown in FIG. 11 or the ICD 600 can also be adapted to provide the waveform similar to the waveform shown in FIG. 11, adapted for cardioversion or atrial defibrillation or it, in addition to a defibrillation waveform, similar to the waveform of FIG. 2, adapted for ventricular defibrillation. This embodiment of the present invention is therefore capable of providing both a lower pain cardioversion waveform, where the discomfort experienced by the patient during cardioversion or atrial defibrillation is reduces as a result of the leading and trailing edges of the waveform being rounded or a biphasic defibrillation waveform. The waveforms of this embodiment are preferably biphasic so as to increase the efficacy of the therapy being delivered.

The exact configuration of the ICD implanted within the patient will, of course, vary depending upon the individual needs of the patient. In one embodiment, the capacitors are 300 microfarad capacitors that are charged to a peak voltage of approximately 400 volts. The resistor Rf is approximately 10 ohms and the resistor Rd is approximately 5 ohms.

Although the foregoing description of the preferred embodiments of the present invention has shown, described and pointed out the fundamental novel features of the invention, it will be understood that various omissions, substitutions and changes in the form of the detail of the apparatus as illustrated as well as the uses thereof, may be made by those skilled in the art, without departing from the spirit of the present invention. Consequently, the scope of the invention should not be limited to the foregoing discussion, but should be defined by the appended claims.

What is claimed is:

1. An implantable electrical device for providing therapeutic shocks to the heart, the device comprising:

a controller that is adapted to receive a sense signal indicative of the function of the heart and provide a plurality of output signals in response thereto;

an output circuit that is adapted to provide cardioversion shocks to the heart via leads wherein the output circuit is configurable in response to signals from the controller so as to be able to apply a first waveform to the heart, wherein the first waveform is adapted to perform cardioversion, including atrial defibrillation or VF induction of the heart, wherein the first waveform is adapted to be biphasic with the leading and trailing edges of the biphasic waveform being rounded.

2. The device of claim 1, wherein the output circuit comprises an H-bridge connected to the leads wherein the H-bridge is adapted to provide a positive portion of the first waveform to the leads at a time T1 and a negative portion of the waveform to the heart at a time T4.

3. The device of claim 1, wherein the output circuit comprises:

a first capacitor which is adapted to be connected to leads which provide therapeutic shocks to the heart;

a second capacitor connected in parallel with the first capacitor;

a first resistor and a first controllable switch connected to the positive node of the first capacitor between the positive node of the first and second capacitor wherein the first controllable switch is adapted to simultaneously connect the first capacitor to the leads and to the second capacitor at the time T1 to thereby simultaneously apply energy to the leads and also to charge the second capacitor.

4. The device of claim 3, wherein the controller is adapted to provide signals to the first controllable switch at a time T2 so as to disconnect the first capacitor from the leads so that the leads only receive the stored energy from the second capacitor.

5. The device of claim 4, wherein the output circuit further comprises a second resistor and a second controllable switch that are connected in parallel with the first capacitor, the second capacitor and the H-bridge so as to be interposed between the first and second capacitors and the H-bridge and wherein the controller provides output signals so as to induce the second switch to connect the second resistor is parallel with the H-bridge at a time T3 so that the trailing edge of the positive portion of the first cardioversion waveform is rounded.

6. The device of claim 5, wherein the controller is adapted to manipulate the first switch at the time T4 so that the first capacitor is simultaneously reconnected to the second capacitor and the leads and also manipulate the second switch so as to disconnect the second resistor from the circuit attached to the leads.

7. The device of claim 6, wherein the controller is adapted to manipulate the first switch at a time T5 so that only the second capacitor is connected to the H-bridge.

8. The device of claim 7, wherein the controller is adapted to manipulate the second switch at a time T6 so as to connect the second resistor to the output circuit that is applied to the H-bridge to thereby produce a rounded trailing edge of the negative portion of the first waveform.

9. The device of claim 3, wherein the output circuit further comprises at least one defibrillation switch that directly connects the first and second capacitors in series so that the first and second capacitors can be applied directly to the leads to thereby allow the leads to provide a second waveform to the heart that is adapted to provide ventricular defibrillation.

10. An implantable electrical device for providing therapeutic shocks to the heart, the device comprising:

a controller that receives a sense signal indicative of the function of the heart and provides a plurality of output signals in response thereto;

an output circuit that is adapted to provide therapeutic shocks to the heart wherein the output circuit is configurable, in response to output signals from the controller, into a first configuration wherein a first therapeutic shock having a first waveform is applied to the heart and into a second configuration wherein a second therapeutic shock having a second waveform is applied to the heart wherein the first waveform is configured to accomplish ventricular defibrillation of the heart and the second waveform is configured to perform cardioversion, including atrial defibrillation or VF induction of the heart, wherein the second waveform is adapted to be biphasic with the leading and trailing edges of the biphasic waveform being rounded.

11. The device of claim 10, wherein the output circuit comprises:

at least one capacitor that is adapted to be charged in response to an output signal from the controller so that a voltage can be applied to the heart from the capacitor;

a resistor that can be interposed between the heart and the capacitor so as to be in series therewith;

at least one switch that operates in response to the output signals from the controller wherein operation of the switch results in the resistor being positioned in series with the heart, between the capacitor and the heart, when the second waveform is being applied to the heart.

12. The device of claim 11, wherein the output circuit comprises:

a first capacitor;

a first resistor connected to the positive node of the first capacitor;

a second capacitor that is connected to the first resistor so as to be in parallel with the first capacitor; and an H-bridge that applies a biphasic waveform to the heart of the patient that is connected in parallel to the first and second capacitors.

13. The device of claim 12, wherein the at least one controllable switch of the output circuit is connected so that the controller can induce voltage from the first capacitor to the H-bridge and also to the second capacitor at a time T1 so as to charge the second capacitor and the at least one controllable switch is also connected so that the controller can configure the output circuit so that the first capacitor is disconnected from the H-bridge at a time T2 so that the H-bridge only receives the voltage from the charged second capacitor.

14. The device of claim 13, wherein the at least one controllable switch is connected in series with the first resistor between the positive nodes of the first and second capacitors.

15. The device of claim 14, wherein the output circuit further comprises a second resistor and a second controllable switch that are connected so as to be in parallel with the H-bridge and the first and second capacitors.

16. The device of claim 15, wherein the controller is adapted to operate the second controllable switch at a time T3 so that the second resistor is in parallel with the H-bridge so that a trailing edge of the cardioversion waveform is more rounded.

17. The device of claim 10, wherein the output circuit also includes at least one controllable switch that is adapted to connect the first and second capacitors in series during application of the defibrillation waveform in response to a signal from the controller.

18. The device of claim 17, wherein the output circuit also includes at least one switch that is adapted to apply the combined stored voltage of the first and second capacitors directly to the H-bridge in response to a signal from the controller.

19. An implantable electrical device for providing therapeutic shocks to the heart the device comprising:

delivery means for delivering a first therapeutic waveform to the heart;

control means for controlling the delivery of the first therapeutic waveform to the heart;

waveform generation means for developing the first therapeutic waveform, wherein the waveform generation means is adapted to generate a biphasic waveform adapted for cardioversion, wherein the biphasic waveform has rounded trailing and leading edges so as to reduce the discomfort experienced by the patient in whom the device is implanted.

20. The device of claim 19, wherein the waveform generation means is comprised of an output circuit that includes:

an H-bridge that is coupled to the delivery means wherein the H-bridge is controlled by the control means so as to produce a biphasic waveform;

a first capacitor that is connected in parallel with the H-bridge;

a second capacitor that is connected in parallel with the H-bridge and the first capacitor; and a first switch interposed between the first and second capacitors.

21. The device of claim 20, wherein the control means, at a time T1, configures the H-bridge so that a positive portion of the waveform will be applied to the deliver means and wherein the control means also configure the first switch so that the first capacitor is simultaneously connected to the second capacitor and the H-bridge.

22. The device of claim 21, wherein the control means, at a time T2, configure the first switch so that the first capacitor is no longer connected to the H-bridge.

23. The device of claim 22, wherein the output circuit further includes a second switch and a resistor, wherein the second switch and the resistor are connected in parallel with the second capacitor.

24. The device of claim 23, wherein the control means configures the second switch so that the resistor is connected in parallel with the delivery means at a time T3 so that the capacitor discharges through both the resistor and the heart when the device is implanted in the body of a patient thereby producing a more rounded waveform on the trailing edge of the positive portion of the first therapeutic waveform.

25. The device of claim 24, wherein the control means induces the H-bridge to apply a negative portion of the first therapeutic waveform to the delivery means at time T4 and wherein the control means further configures the first switch so that the first capacitor is simultaneously connected to both the second capacitor and to the H-bridge and further configures the second switch so that the resistor is no longer connected in parallel to the H-bridge.

26. The device of claim 25, wherein the control means configures the first switch at a time T5 so that the first capacitor is no longer connected to the H-bridge.

27. The device of claim 26, wherein the control means configures the second switch so that the resistor is connected in parallel to the H-bridge.

28. The device of claim 19, further comprising a defibrillation means for providing a defibrillation waveform to the heart of the patient.

29. The device of claim 28, wherein the waveform generation means is comprised of an output circuit that includes:

an H-bridge that is coupled to the delivery means wherein the H-bridge is controlled by the control means so as to produce a biphasic waveform;

a first capacitor that is connected in parallel with the H-bridge;

a second capacitor that is connected in parallel with the H-bridge and the first capacitor; and a first switch interposed between the first and second capacitors.

30. The device of claim 29, wherein the defibrillation means comprises at least one switch adapted to connect the first and the second capacitors in series and to further connected the first and second capacitors directly to the H-bridge.

* * * * *